United States Patent [19]

Polaschegg

[11] Patent Number: 5,015,226
[45] Date of Patent: May 14, 1991

[54] APPARATUS FOR INFUSION OF MEDICAMENTS

[75] Inventor: Hans-Dietrich Polaschegg, Grünwiesenweg, Fed. Rep. of Germany

[73] Assignee: Fresenius AG, Fed. Rep. of Germany

[21] Appl. No.: 428,811

[22] Filed: Oct. 30, 1989

[30] Foreign Application Priority Data

Nov. 3, 1988 [DE] Fed. Rep. of Germany ....... 3837298

[51] Int. Cl.⁵ ............................................. A61M 37/00
[52] U.S. Cl. ........................................ 604/4; 604/51; 604/66
[58] Field of Search ........................ 604/50, 51, 53, 65, 604/66, 67, 131, 118, 245, 246, 4, 257; 128/DIG. 13

[56] References Cited

U.S. PATENT DOCUMENTS

| | | | |
|---|---|---|---|
| 4,743,228 | 5/1988 | Butterfield | 604/50 |
| 4,747,822 | 5/1988 | Peabody | 604/65 |
| 4,816,019 | 3/1989 | Kamen | 604/65 |
| 4,846,792 | 7/1989 | Bobo, Jr. et al. | 604/50 |
| 4,883,455 | 11/1989 | Leonard | 604/4 |
| 4,898,576 | 2/1990 | Philip | 604/50 |
| 4,964,847 | 10/1990 | Prince | 604/4 |
| 4,968,295 | 11/1990 | Neumann | 604/4 |

Primary Examiner—John D. Yasko
Attorney, Agent, or Firm—Henderson & Sturm

[57] ABSTRACT

For the infusion of medicaments and drugs, in particular heparin, into the partial vacuum region of an extracorporeal blood circuit an apparatus is described which replaces the previously used heparin pump and which comprises a supply container in the form of a syringe, a shutoff member, which may be a clamp, disposed in the feed conduit, a means for measuring the reduced pressure or partial vacuum in the extracorporeal circuit and a control means. Said control means is connected to the pressure measuring means and the shutoff member and constructed for periodic opening and closing of the shutoff member in dependence upon the measured partial vacuum and the desired amount of medicament. The apparatus may be used for example in the extracorporeal blood circuit of a dialysis apparatus.

6 Claims, 2 Drawing Sheets

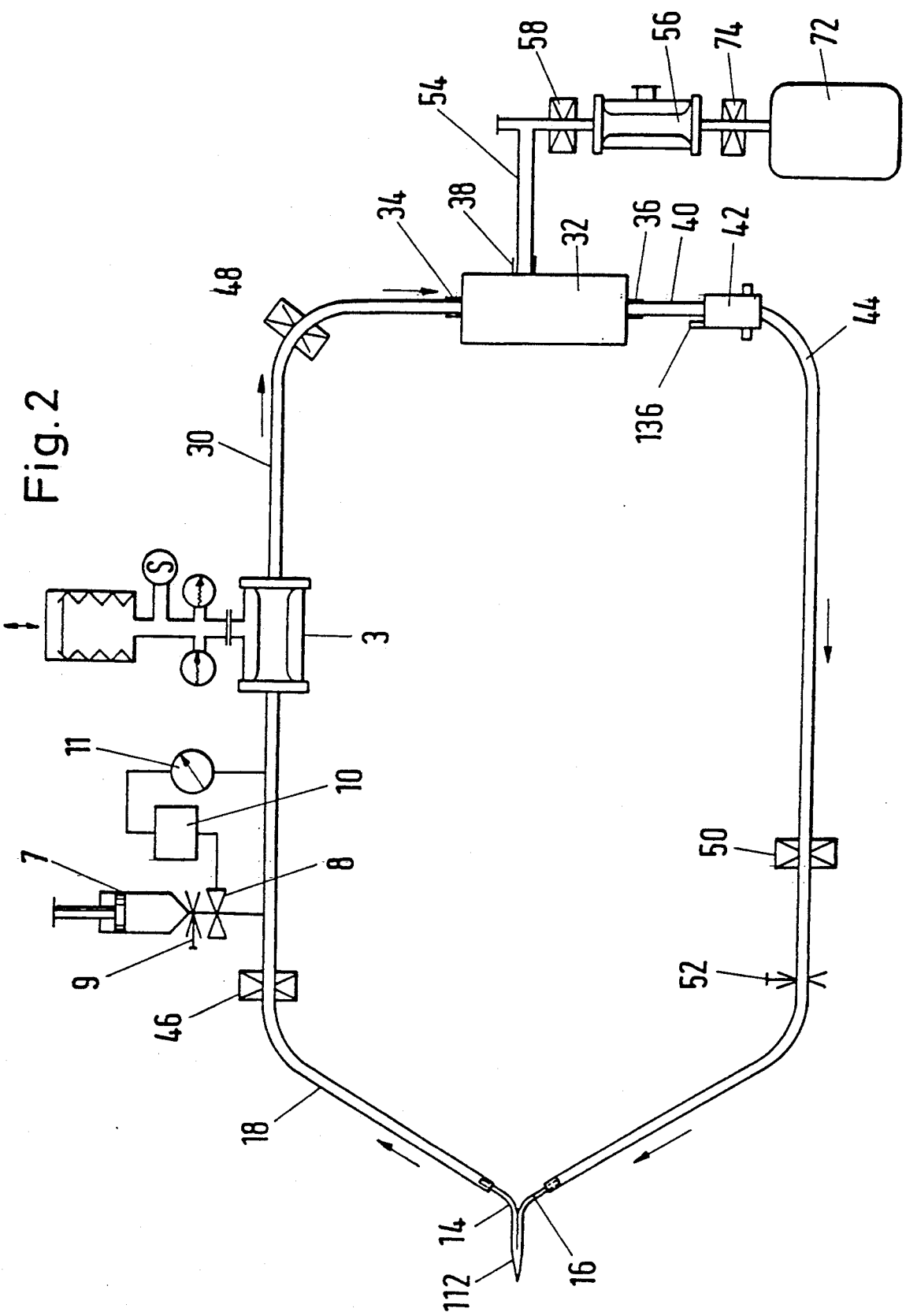

APPARATUS FOR INFUSION OF MEDICAMENTS

BACKGROUND AND SUMMARY OF THE INVENTION

The invention relates to an apparatus for infusion of medicaments, in particular heparin, into the partial vacuum region of an extracorporeal blood circuit, in particular an extracorporeal blood circuit of a dialysis apparatus, comprising a supply container for the medicaments and a feed conduit from the supply container to the extracorporeal blood circuit.

The operation of an extracorporeal blood circuit involves the necessity of inhibiting by addition of suitable medicaments the blood coagulation initiated by contact with the surfaces of the extracorporeal blood circuit. The medicament most frequently used for this purpose is heparin. As a rule, infusion into the blood circuit is carried out continuously and for this purpose either syringe pumps or peristaltic pumps are used. In exceptional cases, if there is a particular danger of hemorrhage, in a dialysis apparatus the effect of the heparin is cancelled again downstream of the blood purifying apparatus by adding another substance, for example prothrombin.

DE-A 2,851,064 admittedly discloses a dosing device for a hemodialysis apparatus which has a water supply valve and separate means, preferably in the form of floats, as known per se but this device is not used to infuse medicaments into the partial vacuum region of an extracorporeal blood circuit because the known device serves to feed dialysate solution previously prepared in special containers into a hemodialysis apparatus. In addition, the aforementioned water supply valve is not arranged in the supply conduit to the extracorporeal circuit but in a water supply conduit lying between a water source and the mixing containers. Finally, since neither a pressure measuring means in the extracorporeal blood circuit nor a control means connected thereto is described this dosing device known from DE-A 2,851,064 is not an apparatus comparable to the apparatus according to the invention.

Finally, DE-A 2,644,062 describes an apparatus for automatic regulation of a hemodialysis apparatus which however teaches the use of pressure measurement only for regulating the speed of a blood pump.

The extensive use of extracorporeal circuits in particular in the field of hemodialysis has led to a large cost burden, in particular on insurance systems, and this in turn has led to a corresponding pressure on the prices of apparatuses and disposable articles. It is therefore the objective of numerous developments to configure the apparatuses constructionally so that without restricting the medical treatment quality or with an improved treatment quality the costs are reduced by reduced material costs and also simpler operation.

The problem underlying the present invention is therefore to provide an apparatus with which it is possible to infuse medicaments into an extracorporeal blood circuit and which for the same treatment quality has a simpler construction than the known apparatuses and is thus more economical to produce.

This problem is solved in an apparatus of the type mentioned at the beginning by the characterizing features of claim 1.

Instead of the heparin pump used hitherto for pumping the corresponding medicament in accordance with a previously defined rate from the supply container into the extracorporeal blood circuit in accordance with the invention said supply container is merely connected to the partial vacuum section of the extracorporeal circuit via a shutoff member which may be a clamp. To actuate said shutoff member, a control means is provided which in dependence upon the partial vacuum obtaining in the extracorporeal blood circuit and the desired medicament rate periodically opens and closes the shutoff member. For measuring the reduced pressure a corresponding measuring means is provided which is arranged downstream of the connection point of the supply or feed conduit in the extracorporeal blood circuit. The control means is connected to said manometer or pressure measuring means. Since in most cases a corresponding pressure measuring device is already present in the extracorporeal blood circuit it is merely necessary to provide an additional connection of this pressure measuring means to the control unit.

The control means is notified of the desired drug or medicament infusion rate via an input device, not shown. Preferably, in the feed conduit either between the medicament supply container and the shutoff member or between the shutoff member and the connection point of the feed conduit to the extracorporeal blood circuit a flow throttle is also incorporated which has a flow resistance which is fixed to take account of the respective medicament viscosity. The control means then controls the clamp in dependence upon the given infusion rate and the partial vacuum measured in such a manner that via the throttle exactly the set amount of medicament flows into the extracorporeal system, the control means being constructed in such a manner that the flow resistance of the throttle or constriction is taken into account.

The apparatus according to the invention can be used in all extracorporeal circuits provided that a partial vacuum obtains in the flexible tube section to which the feed conduit is connected.

In a dialysis apparatus the apparatus according to the invention is arranged in the arterial line of the extracorporeal blood circuit between the patient and blood pump. By the blood pump the necessary partial vacuum is generated which on opening of the shutoff member in the feed conduit leading to the medicament container effects that the medicament solution is aspired from the supply container. By corresponding opening and closing of the shutoff member by means of the control means in this manner the desired amount of medicament is supplied to the extracorporeal blood circuit without an additional pump being necessary as was the case in the prior art.

In extracorporeal circuits operating with a single-needle technique the shutoff member is opened only during the arterial aspiration phase. The control means is constructed in accordance with this purpose.

If the extracorporeal circuit is to be connected via an arterial-venous shunt effecting a positive pressure in the extracorporeal circuit upstream of the pump then by interconnection of a constriction or throttle into the arterial aspiration conduit the necessary partial vacuum can be produced upstream of the blood pump.

DESCRIPTION OF THE DRAWINGS

Examples of embodiment of the invention will be explained in detail hereinafter with the aid of the drawings, wherein:

FIG. 2 is a schematic illustration of the extracorporeal blood circuit of an apparatus for removing water from blood.

DETAILED DESCRIPTION OF A PREFERRED EMBODIMENT OF THE INVENTION

Figure 1:
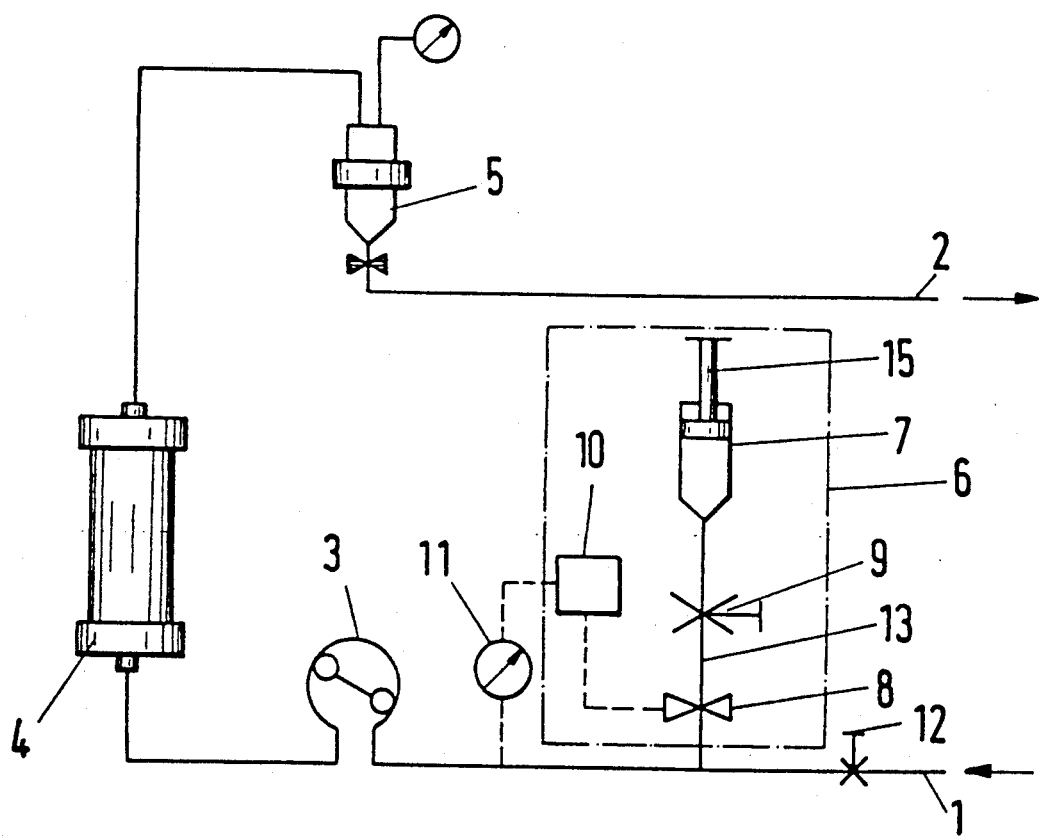
FIG. 1 is a schematic illustration of the extracorporeal blood circuit of a dialysis apparatus.

In FIG. 1 the extracorporeal circuit of a dialysis apparatus is shown. Via the conduit 1 blood is extracted from the patient and is conveyed via a blood pump 3 into the dialyzer 4. From there the purified blood passes via an air separator 5 into the conduit 2 which leads back to the patient. By contact with the surfaces of the extracorporeal circuit blood coagulation is initiated and can be suppressed by adding suitable drugs, for example heparin. For this purpose a medicament supply container 7 is provided which is illustrated in the form of a syringe with a non-fixed plunger 15. Via a supply or feed conduit 13 the desired medicament is supplied to the conduit 1 of the extracorporeal circuit. Since due to the blood pump 3 a partial vacuum continuously obtains in the line section 1 an uncontrolled amount of medicament would be uninterruptedly aspired into the conduit section 1. Therefore, to control the medicament dispensing firstly a flow constriction or throttle 9 and secondly a shutoff member in the form of a clamp 8 are arranged in the feed conduit 13. The arterial monometer 11 present in any case in the extracorporeal circuit is connected to a control unit 10 which on the basis of the desired amount of medicament reported t the control unit 10 via an input device, not shown, and the measured partial vacuum and taking account of the flow resistance of the flow throttle 9 periodically opens and closes the clamp 8 so that the desired amount of medicament is supplied to the extracorporeal circuit.

When the conduit 1 is connected to an arterial-venous shunt there obtains upstream of the pump 3 a certain excess pressure which would prevent the medicament from being able to flow from the supply container 7 into the extracorporeal blood circuit. To generate a partial vacuum in the region of the connection point of the feed conduit 13 an additional flow constriction or throttle 12 is provided upstream. The flow cross-section of said flow throttle 12 is selected so that the blood pump 3 between the flow throttle 12 and the blood pump 3 generates a partial vacuum which causes the medicament to be aspired from the supply container 7 into the extracorporeal blood circuit.

In FIG. 2 an apparatus is shown for removing water from the blood of the patient. This apparatus comprises a hollow cannula 112 with which at one end a blood connection to a vein can be established. The hollow cannula 112 is formed at its other end in Y-shape and thus constitutes two connections 14 and 16 which can be connected to corresponding flexible tube pieces. Said hollow cannula 112 is formed as simple needle which branches accordingly and the mixing effect is practically negligible.

The connection 14 of said hollow cannula 112 serves to carry away blood and is connected to a first tube piece 18. The other end of said tube piece 18 is connected to the blood pump 3. Between the hollow cannula 112 and the blood pump 3 a shutoff member 46 is arranged in the tube piece 18. Between said shutoff member 46 and the blood pump the apparatus according to the invention for the infusion of medicaments is arranged and as has already been described with reference to FIG. 1 consists of the supply container 11, the clamp 8, the flow throttle 9, the control means 10 and the monometer 11.

The pump 3 is connected downstream to a further tube piece 30 which opens into a filter 32. Between the pump 3 and filter 32 a further shutoff member 48 is arranged in the tube piece 30. The filter 32 is constructed as hemofilter and consequently comprises three connections, i.e., the connection 34 connected to the tube piece 30, the outlet 36 and the filtrate outlet 38. The outlet 36 is connected to the tube piece 40 of which the other end communicates with an air separation chamber 42. The air separation chamber 42 is connected via the tube piece 44, a shutoff valve 50 and a throttle means 52 to the hollow cannula 112.

The filtrate outlet 38 is connected via two shutoff members 58 and 74 and a filtrate measuring chamber 56 to the collection bag 72 in which the accumulating filtrate is finally collected.

During operation of this extracorporeal circuit the clamp 46 and the clamp 48 are opened and closed, the clamps 46 and 48 operating in counter cycle. The clamp 50 is controlled analogously to the clamp 48, i.e., in counter cycle to the clamp 46. When the clamp 46 is opened blood is extracted from the patient via the pump 3. At this instant the shut-off member 8 is also opened by the control means 10 so that due to the partial vacuum obtaining in the conduit section 18 the medicament disposed in the supply container 7 is sucked into the extracorporeal circuit. When the clamp 46 is closed and the clamp 48 is opened the shutoff member 8 in the feed conduit 13 is simultaneously also closed. It is possible in this manner during the aspiration phase to add the medicament in the desired dosage to the extracorporeal circuit.

Features and advantages of the invention in addition to those pointed out herein will become apparent to those versed in the art as will many variations in the nature of the invention all without departure from the spirit and scope of the invention.

I claim:

1. Apparatus for infusion of medicaments, in particular heparin, into the partial vacuum region of an extracorporeal blood circuit, in particular an extracorporeal blood circuit of a dialysis apparatus, comprising a supply container for the medicaments and a feed conduit from the supply container to the extracorporeal blood circuit, characterized by a shutoff member arranged in the feed conduit, a pressure measuring means for measuring the partial vacuum in the extracorporeal blood circuit and a control means which is connected to the pressure measuring means and the shutoff member and is constructed for periodic opening and closing of the shutoff member in dependence upon the measured partial vacuum and the desired medicament amount.

2. Apparatus according to claim 1, characterized in that the shutoff member is a clamp.

3. Apparatus according to claim 1 or 2, characterized in that in the feed conduit a flow throttle is arranged.

4. Apparatus according to any one of claims 1 to 3, characterized in that the supply container is a syringe with non-fixed plunger.

5. Apparatus according to any one of claims 1 to 4 infusion of medicaments into an extracorporeal blood circuit with single-needle technique, characterized in that the control means is constructed for opening the shut-off valve during the arterial aspiration phase.

6. Apparatus according to any one of claims 1 to 4 for infusion of medicaments into an extracorporeal blood circuit connected to an arterial-venous shunt, characterized by a further flow throttle which is arranged upstream of the connection point of the feed conduit in the extracorporeal circuit.

* * * * *